United States Patent

Soldevila Domingo et al.

[11] Patent Number: 5,258,742
[45] Date of Patent: Nov. 2, 1993

[54] GAUZE COUNTER APPARATUS FOR SURGICAL USE

[76] Inventors: Jose Soldevila Domingo, C/ Vinyes 9; Jose Grau Galter, C/ Pallars Sobirá 10; Abundio Matias Muñoz, C/Vall d'Aran 7, all of 17500 Ripoll, Girona, Spain

[21] Appl. No.: 850,903

[22] Filed: Mar. 13, 1992

[30] Foreign Application Priority Data

Mar. 14, 1991 [ES] Spain .................................. 9100664

[51] Int. Cl.⁵ .............................................. G08B 21/00
[52] U.S. Cl. ................................... 340/568; 235/98 C; 340/540; 340/74; 604/317
[58] Field of Search ........................ 340/568, 674, 540; 235/98 C, 128; 206/440, 438; 604/317

[56] References Cited

U.S. PATENT DOCUMENTS

| | | | |
|---|---|---|---|
| 2,690,366 | 9/1954 | Kimmel | 108/106 |
| 3,146,944 | 9/1964 | Grippi, Jr. | 235/98 C |
| 3,367,431 | 2/1968 | Baker | 177/15 |
| 4,365,709 | 12/1982 | Lester | 206/362 |
| 4,580,280 | 4/1986 | Hetrick | 235/98 C |
| 4,903,837 | 2/1990 | Duello | 206/440 |

FOREIGN PATENT DOCUMENTS 8520746 10/1985 Fed. Rep. of Germany .
8909563 10/1989 PCT Int'l Appl. .

*Primary Examiner*—Glen R. Swann, III
*Attorney, Agent, or Firm*—Cushman Darby & Cushman

[57] ABSTRACT

A gauze-counting apparatus for surgical use, includes a support frame on is mounted a receiver hopper and a recording chamber. The hopper has a minimum passage section for a single gauze in which is mounted a photoelectric cell, coplanar fashion, the beam of which is broken by the passage of each gauze. The recording chamber includes a power supply, a counter connected to the photoelectric cell, an alarm that is activated when the counter reaches a preset number, and a functioning indicator.

3 Claims, 2 Drawing Sheets

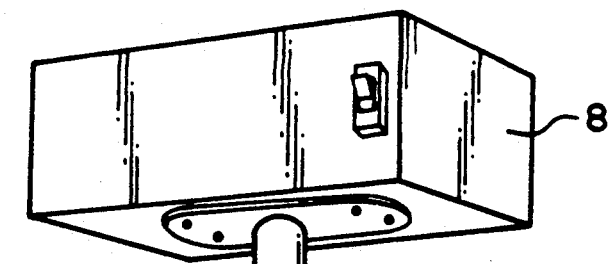
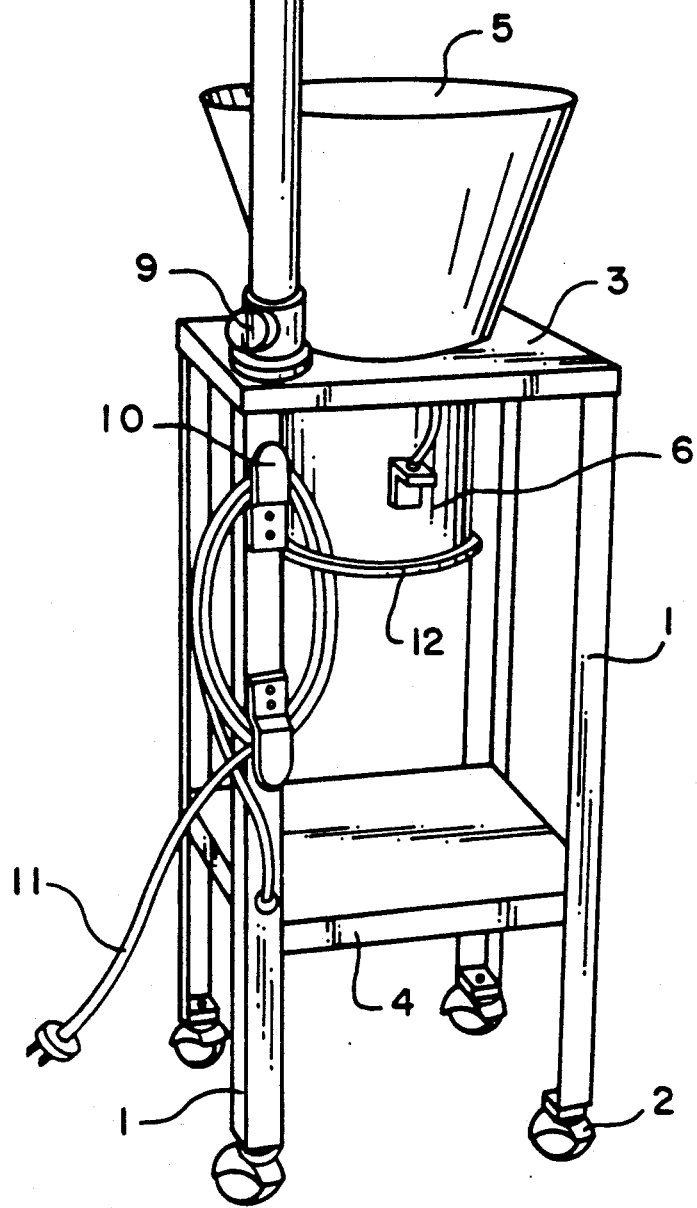

GAUZE COUNTER APPARATUS FOR SURGICAL USE

BACKGROUND OF THE INVENTION

This invention concerns a gauze counting apparatus for surgical use, by means of which quantitative control of the gauzes used during a surgical procedure or operation can be easily and safely carried out.

Control of the gauzes used in the field of surgery is currently done manually by one or more people. For example, the instruments operator may be responsible for counting the gauzes received before the start of the operation and of those that are left unused at the end of that operation. Another person, for example the field nurse, counts the gauzes used in the course of the operation. By means of this system, the number of gauzes used is controlled.

This system assumes that the checking carried out is not the responsibility of the surgeon, who is the one who is actually in charge of the surgical operation or procedure.

Moreover, the control of the gauzes that is done at the end of the operation forces the procedure to come to a halt and, in the best of cases when the result of the count is correct, requires a certain amount of time to be devoted, between 5 and 10 minutes. In the event of the count obtained being incorrect, a circumstance that happens fairly frequently, checking and confirmation have to be carried out again, which can last a much greater length of time. In extreme cases, it will be necessary to check whether any gauze has not been controlled and whether it has even left behind in the operating zone.

A further problem presented by the manual control system discussed above is the possibility of human error in the different counts, so that the counts are given as correct even when they are not. Forgetting an intra-abdominal gauze could have extremely serious consequences, including the death of the patient.

These problems reveal the medical-legal repercussions which correct control of the gauzes used during a surgical procedure can have.

SUMMARY OF THE INVENTION

The subject of the present invention is the development of an apparatus by means of which counting of the gauzes used during an operation can be simply and safely carried out. The apparatus further allows the doctor or surgeon to be aware at all times, and particularly at the end of the operation, of the number of gauzes that have been used and, indeed, to control their number.

The fundamental advantages of the apparatus of the invention are the possibility of checking the control of the gauzes used by the surgeon, immediate and exact knowledge of the number of gauzes used, the fact that the control is being carried out by electronic systems and therefore not subject to human error, and the possibility of setting the apparatus beforehand to the number of gauzes to be used—it will then issue a warning during the surgical procedure when this number of gauzes used has been reached.

Furthermore, the design and handling of the apparatus of the invention is extremely simple, and it can be easily installed in the required place.

The apparatus of the invention includes a support frame on which is mounted a receiver hopper fitted with passage detector means, and a recording chamber, which includes signallers and operating controls.

The receiver hopper will ideally have an inverted truncated conical shape, with a minimum passage section of such a size that allows just one gauze to pass through at a time. In order to achieve this effect, the hopper can be extended, starting from its narrower base, by a cylindrical section containing two oblique partitions which are inclined in a downwards direction and located in diametrically opposite positions. The free edge of these partitions defines a central opening, through which the gauzes will pass, one by one. A further fundamental characteristic of the hopper is that its minimum passage section contains at least one photoelectric cell placed in such a way that the beam emitted by the emitter crosses this minimum section in a coplanar fashion, and is therefore broken every time a gauze drops from the hopper.

The recording chamber houses electrical circuits, including a power supply, an impulse counter connected to the photoelectric cell, an alarm that is activated when the counter reaches a preset number, a functioning indicator and a start-up connector.

BRIEF DESCRIPTION OF THE DRAWINGS

The structure of the apparatus, as well as its characteristics, will be more easily understood with reference to the attached drawings showing a possible way of executing the invention, which is meant as an example only and is not restrictive.

In the drawings:

FIG. 1 is rear elevational view showing a gauze counter apparatus constructed in accordance with the principles of the present invention.

DETAILED DESCRIPTION

Figure 2:
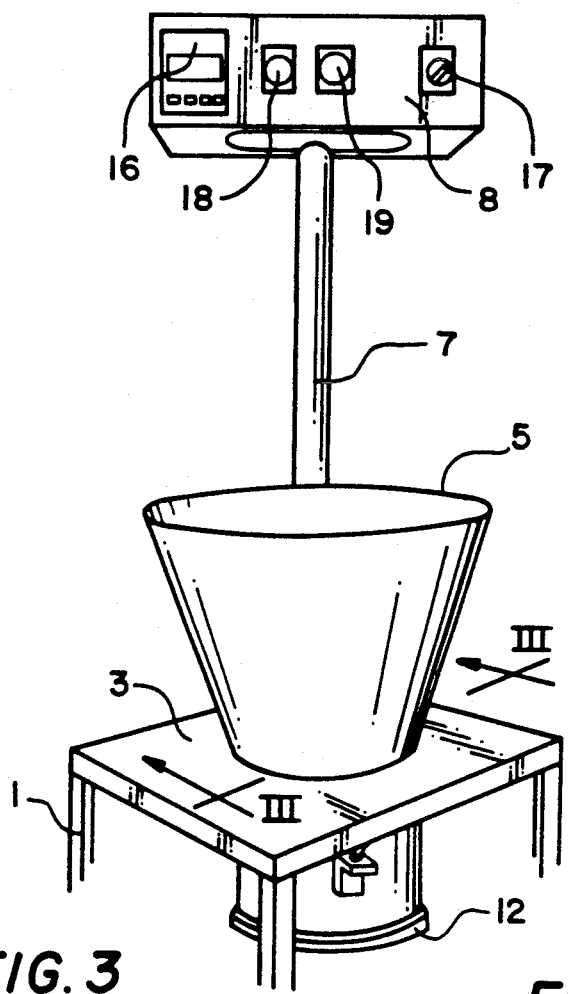
FIG. 2 is a fragmentary front evelational view showing the apparatus of FIG. 1.

As can be seen in FIGS. 1 and 2, the apparatus includes a support frame which has four vertical legs, 1, and supporting wheels 2 at the bottom 2. Mounted between these legs at different heights are two platforms 3 and 4. On the upper platform 3 is mounted a hopper 5 having an inverted truncated conical shape which, starting from the narrower base, is extended by a cylindrical section 6. The platform 3 is thus vertically intersected by the hopper.

Also fixed to the structure so far described, there is a vertical column 7 which supports a recording chamber 8 on its top. The upper tray 3 can be fitted with a vertical collar 9 provided with a pressure screw in order to support the column 7, allowing the height and orientation of the casing 8 to be adjusted.

Ideally, the collar 9 and the column 7 are arranged in a position that is coaxial with one of the legs, which can be fitted with two longitudinal bent lugs 10 pointing in opposite directions. Their purpose is to take the rolled-up connection (i.e., electric power cord) cable 11. This cable can run inside one of the legs of the frame and through the interior of the column 7 and thence reaching the various electronic components.

The bottom of the cylindrical section 6 of the hopper is provided with a peripheral lip 12 that allows the mouth of a bag to be attached, the bottom of which is supported on the lower tray 4.

Figure 3:
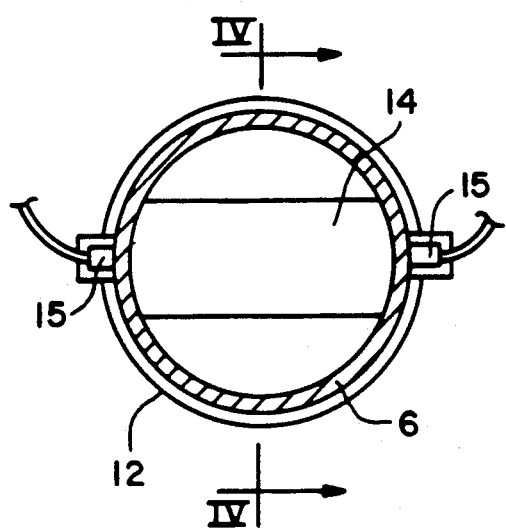
FIG. 3 is a horizontal cross-sectional view taken along the line III—III of FIG. 2.
Figure 4:
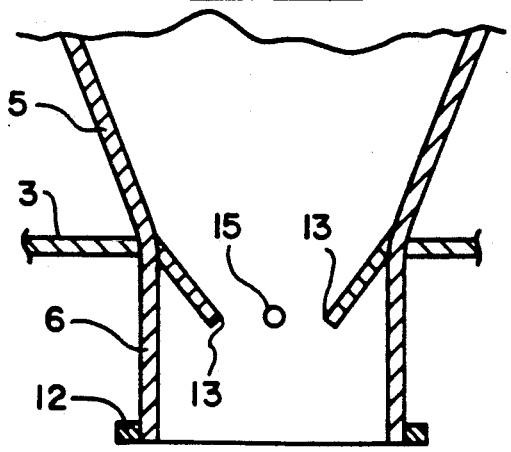
FIG. 4 is a diametric cross-sectional view taken along the line IV—IV of FIG. 3.

The hopper 5 has a minimum passage section defined by two oblique partitions 13, (FIGS. 3 and 4), running in the downwards direction and arranged in diametrically opposite positions, defining a central passage opening 14. Fitted to the side of the cylindrical section 6 of the hopper, and in line with this minimum section 14, is at least one photoelectric cell 15. With this arrangement, the beam emitted by the cell emitter crosses the minimum passage section 14 to be received by a detector, the emitter and detector being arranged in a coplanar fashion horizontally, transversally across the section 6 at the level of the opening 14.

The dector of the photoelectric cell 15 is connected to the circuits housed inside the casing 8, which includes a power supply, an electronic gauze counter 16 which includes an impulse counter connected to the photoelectric cell, a switch that will allow a certain number of gauzes to be memorized, a start-up connector, i.e., 17, a functioning indicator 18 and a breakdown or jam indicator 19.

The hopper 5 is intended to receive the gauzes that are going to be used. The minimum passage section 14 is sized in such a way that only one gauze at a time can pass through it. This gauze will break the beam emitted by the emitter of the photoelectric cell 15, giving out the corresponding impulse which is then recorded in the counter 16.

In this way, the users can at all times be aware of the number of gauzes that are being used.

The apparatus of the invention also allows prior memorization of the number of gauzes that could be expected to be used in a particular operation. When the counter 16 reaches the preset number of gauzes, it emits a signal. This number can be increased at any time.

When the operation ends, the users know precisely the number of gauzes that have been used and whether or not the present number of gauzes has been reached.

We claim:

1. Apparatus for counting gauze bodies used in the course of conducting a surgical procedure on a patient, said apparatus comprising:
   a support frame;
   an upwardly opening, downwardly converging receiving hopper mounted on said support frame; an outlet structure disposed under said hopper on said support frame and arranged such that gauze bodies dropped into said receiving hopper from above drop through said outlet structure;
   said outlet structure including a vertically oriented longitudinal passageway having, at a given level, a transverse cross-sectional shape and size which will permit only one said gauze body at a time to drop down therethrough;
   a photoelectric emitter and detector arranged on said outlet structure to detect gauze bodies dropping through said passageway of said outlet structure at said level; and
   an electrically powered counter mounted on said support frame and operatively connected to said detector for counting gauze bodies detected by said detector.

2. The apparatus of claim 1, further comprising:
   a support platform mounted to said support frame and disposed under said outlet structure; and
   lip means perimetrically provided on said outlet structure, and arranged so that a gauze body collection bag can be supported on said support platform and have a mouth portion thereof perimetrically secured by said lip means to said outlet structure to collect gauze bodies which have dropped through said passageway and been detected and counted by said detector and counter.

3. The apparatus of claim 2, wherein:
   said support frame includes a hollow column which projects upwardly further than does said receiving hopper;
   said counter being mounted to said column and disposed at a second level which is higher than said receiving hopper;
   an electric power cord operatively connected to said counter, passing down internally of said column to a third level which is lower than said receiving hopper and there emerging from said column so as to have an external portion terminating in an electrical plug;
   a set of cord storage wrapping lugs provided on said column, said external portion of said power cord being removably wound around said lugs for storage.

* * * * *